(12) United States Patent
Lopez et al.

(10) Patent No.: US 7,086,864 B2
(45) Date of Patent: *Aug. 8, 2006

(54) ENDODONTIC POST SYSTEM

(75) Inventors: Larry A. Lopez, 522 Pleasant Valley Dr. North, Boerne, TX (US) 78006; Bruce A. Finnigan, Wallingford, CT (US); Ajit Karmaker, Wallingford, CT (US); Bruce Alpert, Madison, CT (US); Weitao Jia, Wallingford, CT (US)

(73) Assignees: Pentron Clinical Technologies, LLC, Wallingford, CT (US); Larry A. Lopez, Boerne, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/164,512

(22) Filed: Jun. 6, 2002

(65) Prior Publication Data
US 2004/0248067 A1 Dec. 9, 2004

Related U.S. Application Data

(63) Continuation-in-part of application No. 09/684,493, filed on Oct. 6, 2000, now Pat. No. 6,428,316, which is a continuation-in-part of application No. 09/571,040, filed on May 12, 2000, now Pat. No. 6,447,297.

(60) Provisional application No. 60/133,733, filed on May 12, 1999.

(51) Int. Cl.
*A61C 5/02* (2006.01)

(52) U.S. Cl. .................................................... 433/224
(58) Field of Classification Search ................ 433/224, 433/220, 221, 225, 81
See application file for complete search history.

(56) References Cited

U.S. PATENT DOCUMENTS 277,943 A  5/1883  Richmond (Continued)

FOREIGN PATENT DOCUMENTS

DE  34 08 503 A1  9/1984

(Continued)

OTHER PUBLICATIONS

PCT Notification of Transmittal of the International Search Report or the Declaration with date of mailing Aug. 17, 2000.

(Continued)

*Primary Examiner*—Cary E. O'Connor
(74) *Attorney, Agent, or Firm*—Ann M. Knab

(57) ABSTRACT

An endodontic post comprising a combined endodontic post and filling material tip in a single unit. To use the post unit, the device is placed in an oven or heater to heat and soften the thermoplastic material. The device will then be placed in a root canal that has been opened to a predetermined dimension by use of endodontic files, to seal the apical end. If necessary, the gutta percha can be compacted toward the apex, while it is still in the softened state, to ensure the apex is adequately sealed. The post is then cemented into place by lining the canal walls with a bonding agent and filling the interface between the post and the walls of the canal with a dual cure resin cement. This will result in a coronal seal of the canal via resin restorative material and an apical seal of the canal by means of gutta percha and sealant. The remaining portion of the post, extending supra-gingivally, will be used to build a core around it. Any excess will be cut off. One length of the device will be longer to accommodate the longer roots in anterior teeth. Another length will be shorter to accommodate smaller roots in the molar region.

27 Claims, 3 Drawing Sheets

U.S. PATENT DOCUMENTS

| | | |
|---|---|---|
| 674,419 A | 5/1901 | Kinsman |
| 1,312,120 A | 8/1919 | Hurtt |
| 1,463,963 A | 8/1923 | Miller |
| 1,469,992 A | 10/1923 | Card |
| 1,641,844 A | 9/1927 | Fisher |
| 1,649,508 A | 11/1927 | Carmichael |
| 3,066,112 A | 11/1962 | Bowen |
| 3,179,623 A | 4/1965 | Bowen |
| 3,194,784 A | 7/1965 | Bowen |
| 3,318,000 A | 5/1967 | Paris |
| 3,504,438 A | 4/1970 | Wittman et al. |
| 3,740,851 A | 6/1973 | Weissman |
| 3,751,399 A | 8/1973 | Lee, Jr. et al. |
| 3,813,779 A | 6/1974 | Tostl |
| 3,855,702 A | 12/1974 | Malmin |
| 3,899,830 A | 8/1975 | Malmin |
| 3,919,774 A | 11/1975 | Fishman |
| 3,926,906 A | 12/1975 | Lee, II et al. |
| 3,949,479 A | 4/1976 | Malmin |
| 3,968,567 A | 7/1976 | Nevins |
| 4,050,156 A | 9/1977 | Chasanoff et al. |
| 4,253,829 A | 3/1981 | Adelberger |
| 4,253,835 A | 3/1981 | Ware |
| 4,343,608 A | 8/1982 | Hodosh |
| 4,407,675 A | 10/1983 | Hodosh |
| 4,425,094 A | 1/1984 | Tateosian et al. |
| 4,480,996 A | 11/1984 | Crovatto |
| 4,480,998 A | 11/1984 | Carse |
| 4,505,675 A | 3/1985 | Albert |
| 4,505,676 A | 3/1985 | Gonser |
| 4,518,356 A | 5/1985 | Green |
| 4,525,147 A | 6/1985 | Pitz et al. |
| 4,538,989 A | 9/1985 | Apairo, Jr. et al. |
| 4,543,065 A | 9/1985 | Bushway |
| 4,544,359 A | 10/1985 | Waknine |
| 4,547,531 A | 10/1985 | Waknine |
| 4,622,012 A | 11/1986 | Smoler |
| 4,657,592 A | 4/1987 | Takubo |
| 4,681,545 A | 7/1987 | Lapcevic |
| 4,682,949 A | 7/1987 | Warrin |
| 4,684,555 A | 8/1987 | Neumeyer |
| 4,717,341 A | 1/1988 | Goldberg et al. |
| 4,721,735 A | 1/1988 | Bennett et al. |
| 4,738,616 A | 4/1988 | Reynaud |
| 4,740,245 A | 4/1988 | Futami et al. |
| 4,746,292 A | 5/1988 | Johnson |
| 4,758,156 A | 7/1988 | Johnson |
| 4,766,200 A | 8/1988 | Riazi |
| 4,801,528 A | 1/1989 | Bennett |
| 4,813,876 A | 3/1989 | Wang |
| 4,820,152 A | 4/1989 | Warrin et al. |
| 4,871,312 A | 10/1989 | Heath |
| 4,882,407 A | 11/1989 | Riazi |
| 4,894,011 A | 1/1990 | Johnson |
| 4,894,012 A | 1/1990 | Goldberg et al. |
| 4,931,096 A | 6/1990 | Fujisawa et al. |
| 4,934,934 A | 6/1990 | Arpaio, Jr. et al. |
| 4,936,775 A | 6/1990 | Bennett |
| 4,936,776 A | 6/1990 | Kwiatkowski |
| 4,950,697 A | 8/1990 | Chang et al. |
| 4,952,150 A | 8/1990 | Schiwiora et al. |
| 4,966,952 A | 10/1990 | Riaza |
| 4,986,754 A | 1/1991 | Chang et al. |
| 5,051,093 A | 9/1991 | Fitzmorris |
| 5,064,373 A | 11/1991 | Staubli et al. |
| 5,067,900 A | 11/1991 | McSpadden |
| 5,073,112 A | 12/1991 | Weil |
| 5,074,792 A | 12/1991 | Bernadat |
| 5,083,923 A | 1/1992 | McSpadden |
| 5,085,586 A | 2/1992 | Johnson |
| 5,088,927 A | 2/1992 | Lee |
| 5,089,183 A | 2/1992 | Johnson |
| 5,092,773 A | 3/1992 | Levy |
| 5,098,298 A | 3/1992 | Johnson |
| 5,104,321 A | 4/1992 | Filhol |
| 5,106,298 A | 4/1992 | Heath et al. |
| 5,118,297 A | 6/1992 | Johnson |
| 5,149,268 A | 9/1992 | Johnson |
| 5,161,973 A | 11/1992 | Johnson |
| 5,165,893 A | 11/1992 | Thompson |
| 5,171,146 A | 12/1992 | Guerci |
| 5,181,850 A | 1/1993 | Neumeyer |
| 5,190,702 A | 3/1993 | Johnson |
| 5,215,461 A | 6/1993 | Riazi |
| 5,232,440 A | 8/1993 | Wilk |
| RE34,439 E | 11/1993 | Heath |
| 5,275,562 A | 1/1994 | McSpadden |
| 5,276,068 A | 1/1994 | Waknine |
| 5,286,193 A | 2/1994 | Roane |
| 5,286,423 A | 2/1994 | Johnson |
| 5,302,129 A | 4/1994 | Heath et al. |
| 5,326,263 A | 7/1994 | Weissman |
| 5,328,367 A | 7/1994 | Johnson |
| 5,328,372 A | 7/1994 | Reynaud et al. |
| 5,372,759 A | 12/1994 | Johnson |
| 5,380,200 A | 1/1995 | Heath et al. |
| 5,382,161 A | 1/1995 | Roane |
| 5,395,240 A | 3/1995 | Paschke et al. |
| 5,409,378 A | 4/1995 | Pohl |
| 5,415,547 A | 5/1995 | Torabinejad et al. |
| RE35,070 E | 10/1995 | Fitzmorris |
| 5,464,362 A | 11/1995 | Heath et al. |
| 5,518,399 A | 5/1996 | Sicurelli, Jr. et al. |
| RE35,264 E | 6/1996 | Bennett |
| 5,527,205 A | 6/1996 | Heath et al. |
| 5,540,766 A | 7/1996 | Castellani |
| 5,564,929 A | 10/1996 | Alpert |
| 5,588,835 A | 12/1996 | Kert |
| 5,595,486 A | 1/1997 | Manocha |
| 5,605,460 A | 2/1997 | Heath et al. |
| 5,624,259 A | 4/1997 | Heath et al. |
| 5,624,976 A | 4/1997 | Klee |
| 5,628,674 A | 5/1997 | Heath et al. |
| 5,648,403 A | 7/1997 | Martin |
| 5,653,590 A | 8/1997 | Heath et al. |
| 5,655,950 A | 8/1997 | Heath et al. |
| 5,713,736 A | 2/1998 | Heath et al. |
| 5,741,139 A | 4/1998 | Sicurelli, Jr. et al. |
| 5,752,825 A | 5/1998 | Buchanan |
| 5,756,559 A | 5/1998 | Blackwell et al. |
| 5,762,497 A | 6/1998 | Heath |
| 5,762,541 A | 6/1998 | Heath et al. |
| 5,769,638 A | 6/1998 | Torabinejad et al. |
| 5,797,748 A | 8/1998 | Reynaud et al. |
| 5,803,736 A | 9/1998 | Merritt, Jr. |
| 5,807,106 A | 9/1998 | Heath |
| 5,816,816 A | 10/1998 | Scharf |
| 5,833,457 A | 11/1998 | Johnson |
| 5,833,464 A | 11/1998 | Foser |
| 5,882,196 A | 3/1999 | Kert |
| 5,915,970 A | 6/1999 | Sicurelli, Jr. et al. |
| 5,919,044 A | 7/1999 | Sicurelli, Jr. et al. |
| 5,921,775 A | 7/1999 | Buchanan |
| 5,925,179 A | 7/1999 | Mannschedel |
| 5,941,760 A | 8/1999 | Heath et al. |
| 5,948,129 A | 9/1999 | Nonami et al. |
| 5,989,032 A | 11/1999 | Reynaud et al. |
| 6,010,335 A * | 1/2000 | Kert ............................ 433/81 |
| 6,012,924 A | 1/2000 | Reynaud et al. |
| 6,024,565 A | 2/2000 | Sicurelli et al. |
| 6,024,569 A | 2/2000 | Ohne et al. |
| 6,028,125 A | 2/2000 | Combe et al. |
| 6,030,220 A | 2/2000 | Karmaker et al. |
| 6,039,569 A | 3/2000 | Prasad et al. |

| | | | |
|---|---|---|---|
| 6,074,209 | A | 6/2000 | Johnson |
| 6,106,296 | A | 8/2000 | Johnson |
| 6,120,294 | A | 9/2000 | Engelbrecht et al. |
| 6,126,446 | A | 10/2000 | Mannschedel |
| 6,162,056 | A | 12/2000 | Mannschedel |
| 6,183,253 | B1 | 2/2001 | Billet et al. |
| 6,186,791 | B1 | 2/2001 | Karmaker et al. |
| 6,214,048 | B1 | 4/2001 | Ito et al. |
| 6,220,863 | B1 | 4/2001 | Kamohara et al. |
| 6,224,377 | B1 | 5/2001 | Bachmann et al. |
| 6,254,392 | B1 | 7/2001 | Mannschedel et al. |
| 6,261,099 | B1 | 7/2001 | Senia et al. |
| 6,264,471 | B1 | 7/2001 | Martin |
| 6,267,597 | B1 | 7/2001 | Kim |
| 6,287,122 | B1 | 9/2001 | Seeram et al. |
| 6,293,795 | B1 | 9/2001 | Johnson |
| 6,371,763 | B1 | 4/2002 | Sicurelli, Jr. et al. |
| 6,428,319 | B1 | 8/2002 | Lopez et al. |
| 6,447,297 | B1 | 9/2002 | Lopez et al. |
| 6,455,608 | B1 | 9/2002 | Jia et al. |
| 6,461,420 | B1 | 10/2002 | Ikuta |
| 6,472,454 | B1 | 10/2002 | Qian |
| 4,758,156 | C1 | 11/2002 | Johnson |
| 6,537,563 | B1 | 3/2003 | Jia et al. |
| 6,566,418 | B1 | 5/2003 | Imai et al. |
| 6,568,937 | B1 | 5/2003 | Kamohara et al. |
| 6,787,584 | B1 | 9/2004 | Jia et al. |
| 2002/0019456 | A1 | 2/2002 | Jia |
| 2002/0072035 | A1 | 6/2002 | Hickok |
| 2002/0142261 | A1 | 10/2002 | Van Den Houdt |
| 2002/0147249 | A1 | 10/2002 | Klee et al. |
| 2002/0198283 | A1 | 12/2002 | Imai et al. |
| 2003/0045604 | A1 | 3/2003 | Klee |
| 2003/0113686 | A1 | 6/2003 | Jia et al. |
| 2003/0124483 | A1 | 7/2003 | Jia et al. |
| 2003/0207960 | A1 | 11/2003 | Jia |
| 2004/0115589 | A1 | 6/2004 | Karmaker et al. |
| 2004/0249015 | A1 | 12/2004 | Jia et al. |
| 2004/0265783 | A1 | 12/2004 | Karmaker et al. |
| 2005/0003328 | A1 | 1/2005 | Karmaker et al. |
| 2005/0066854 | A1 | 3/2005 | Jia et al. |
| 2005/0069836 | A1 | 3/2005 | Jia et al. |

FOREIGN PATENT DOCUMENTS

| | | |
|---|---|---|
| DE | 35 04 472 A1 | 7/1986 |
| DE | 35 12 938 A1 | 10/1986 |
| DE | 35 13 864 A1 | 10/1986 |
| DE | 38 39 466 C2 | 6/1989 |
| DE | 41 03 355 A1 | 6/1992 |
| EP | 0 329 098 B1 | 2/1989 |
| EP | 0 539 751 A1 | 10/1992 |
| FR | 557 756 | 5/1923 |
| FR | 1 180 326 | 12/1958 |
| FR | 2 616 653 | 6/1987 |
| FR | 2 669 211 | 5/1992 |
| FR | 2730 627 | 8/1996 |
| GB | 1412077 | 10/1975 |
| WO | WO 93/14714 | 8/1993 |
| WO | WO/9319687 | 10/1993 |
| WO | WO 98/11842 | 3/1998 |
| WO | WO 00/67659 | 11/2000 |
| WO | WO 02/078646 | 10/2002 |
| WO | WO 2004/037214 A1 | 5/2004 |

OTHER PUBLICATIONS

PCT Written Opinion with date of mailing Jan. 26, 2001.
Notification of Transmittal of the International Preliminary Examining Report with date of mailing Oct. 4, 2001.
Notification of Transmittal of the International Prelliminary Examination Report with date of mailing Jan. 24, 2005.
PCT Notification of Transmittal of the International Search Report and the Written Opinion of the International Searching Authority, or the Declaration with date of mailing Apr. 1, 2005.
Soft Core Dental Products Information "Soft Core" [http://www.variodent.at/grossha/022000/soft-core.html] May 2001.
Product Information for Tone P757 Polymer, Form No. 321.00050, Dow Chemical Company, Dec. 2001.
Product Information for Tone P767 Polymer, Form No. 321-00051, Dow Chemical Company, Dec. 2001.
Product Information for Tone P787, Polymer, Form No. 321-00052, Dow Chemical Company, Dec. 2001.
Shipper G., Orstavik D., Teixeira F.B., Trope M., An Evaluation of Microbial Leakage in Roots Filled with a Termoplastic Synthetic Polymer-Based Root Canal Filling Material (Resilon),Journal of Endodontics, vol. 30, No. 5, May 2004, pp. 342-347.
Teixeira F.B., Teixeira E.C.N., Thompson J.Y., Trope M., "Fracture Resistance of Roots Endodo tically Treated with a New Resin Filling Material", JADA 2004; 135:646-652.
Nahmias Y., Serota K.S., Watson, Jr. W.R., "Predictable Endodontic Success: Part II—Microstructural Replication", Oral Health Journal, Dec. 2003.
Mounce R., Glassman G., "Bonded Endodontic Obturation: Another Quantum Leap Forward for Endodontics", Oral Health Journal, Jul. 2004.
Chivian N., "Resilon—The Missing Link in Sealing the Root Canal", Compendium, vol. 25, No. 10A, Oct. 2004, pp. 823-825.
Barnett F., Trope M., Adhesive Endodontics: Combining Technologies for Enhanced success:, Dentaltown, vol. 5, Issue 8, Aug. 2004, pp. 34,36,38.
Goff, S., "Easier Endo, A DPR Survey report", Dental Products Report, Sep. 2004, pp. 14,15,16,17,18,20.
Shipper, G, Teixeira, F.B., Arnold, RR, Trope, M, "Periapical Inflammation after Coronal Microbial Innoculation of Dog Roots Filled with Gutta-Percha or Resilon", Journal of Endonontics, vol. 31, No. 2, Feb. 2005, pp. 91-96.
Dentsply Product Information "Thermasystem Plus Obturation System", [http://www.xray.essix.comendodontics/endomain.html]May 2001.
Dentsply Product Information "DENSFIL" [http://ww.maillefer.com/html/obturation.html]May 2001.
PCT NotificationofTransmittal of the International Search Report or the Declaration with date of mailing Nov. 6, 2003.
PCT Written Opinion with date of mailing Jun. 15, 2004.
PCT Written Opinion with date of mailing Nov. 5, 2004.
Stratton et al., "A Fluid Filtration Comparison of Gutta-Percha Versus Resilon: A New Soft Resin Endodontic Obturation System", Abstract #20, 31(3) Mar. 2005, Journal of Endodontics.
Alongi DJ, Calcedo R, Moiseyeva R, Vo K, Sarkar, NK, "Interfaces in Soft Resin Obturated Root Canals", Abstract: 2005 IADR/AADR/CADR 83rd General Session & Exhibition.
Tay FR, Loushine RJ, Weller RN, Kimbrough WF, Pashley DH, Mak YF, Lai CNS, Raina R, Williams MC, "Bonding of Self-Etching Primer/Polycaprolactone-Based Root-Filling Material to Intraradicular Dentin", Abstract: 2005 IADR/AADR/CADR 83rd General Session & Exhibition.
Jia W, Gagliardi S, Jin S, "Bondability of Resilon to a Root Canal Sealant", Abstract: 2005 IADR/AADR/CADR 83rd General Session & Exhibition.

Li Y, Zhang W, Onyago O, Jia W, Gagliardi S, "Antimicrobial Potential of Epiphany RCS System", Abstract: 2005 IADR/AADR/CADR 83rd General Session & Exhibition.

Benzley LP, Liu, JCH, Williamson, AE, "Characterization of Tubule Penetration Using Resilon: A Soft-Resin Obturation System", Abstract: 2005 IADR/AADR/CADR 83rd General Session & Exhibition.

Barnett, F, Trope M, "Resilon: A Novel Material to Replace Gutta Percha", Contemporary Esthetics and Restorative Practice, Aug. 2005, vol., 9, No. 8, pp. 64-67.

Gambarini G, Pongione G, "Apical Leakage of a New Obturation Technique", Abstract #42, 31(3), Mar. 2005, Study by Gambarini and Pongione in the Journal of Endodontics.

* cited by examiner

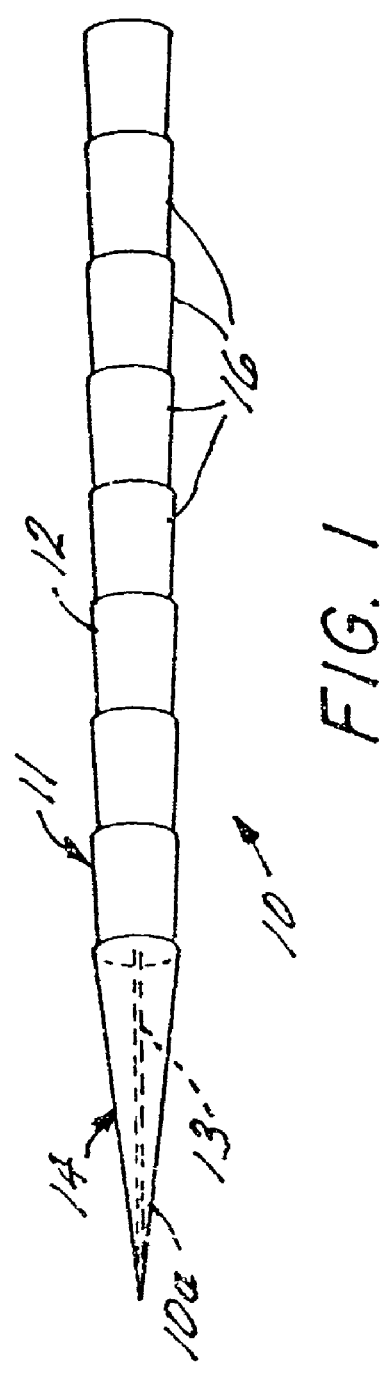
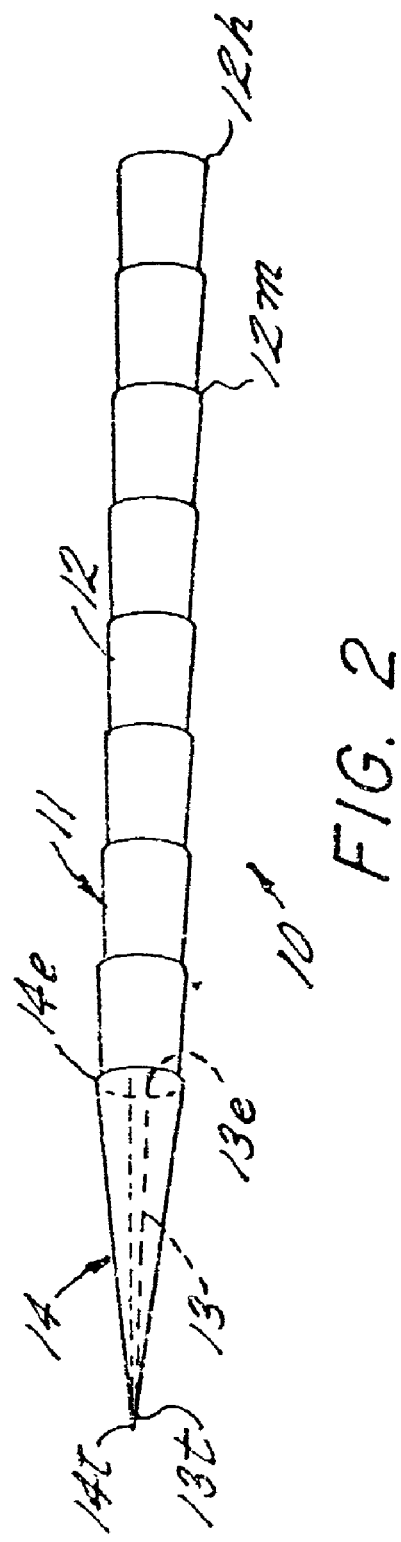

ENDODONTIC POST SYSTEM

CROSS-REFERENCE TO RELATED APPLICATIONS

This application is a continuation-in-part application of U.S. patent application Ser. No. 09/684,493 filed Oct. 6, 2000, now U.S. Pat. No. 6,428,319 which is a continuation-in-part application of U.S. patent application Ser. No. 09/571,040, filed May 12, 2000, now U.S. Pat. No. 6,447,297 which claims priority to U.S. Provisional Application No. 60/133,733, filed May 12, 1999, which are all incorporated herein by reference.

FIELD OF THE INVENTION

This invention relates to both the obturation of a root canal having undergone endodontic treatment and the simultaneous placement of an endodontic post system.

BACKGROUND OF THE INVENTION

Endodontics or root canal therapy is that branch of dentistry that deals with the diseases of the dental pulp and associated tissues. One aspect of endodontics comprises the treatment of infected root canals, the removal of diseased pulp tissues, followed by the biomechanical modification and the subsequent filling of the pulp canal (root canal). Root canal therapy is generally indicated for teeth having sound external structures but having diseased, dead or dying pulp tissues. Such teeth may or may not generally possess intact enamel and dentin and are satisfactorily engaged with bony tissue. In such teeth, the pulp tissue and excised portions of the root should be replaced by a biocompatible substitute.

One technique for the preparation of a root canal involves creating a coronal access opening with a conventional dental drill. A tool is used for gross removal of pulp material from the root canal through the coronal access opening. The void formed is enlarged with reamers and/or files to result in a fully excavated cavity. Debris is removed from this cavity by flushing and the cavity is cleansed to remove all diseased tissue. Following chemical antisepsis, the excavated canal is ready for filling.

A basic method involves inserting a filling cone into a root canal and cementing therein to obturate the canal. Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones. Vertical condensation of warm or hot gutta percha is yet another method of sealing root canals. After cementing a primary cone short of the apex of the root canal, heat application is alternated with a series of smaller and smaller pluggers until the gutta percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta percha. Alternatively, small segments of gutta percha can be used in this method that are inserted into the root canal, heated in order they can adhere to one another and each backfilled one at a time until the root canal is filled. All three of these methods, the single filling cone, lateral condensation and vertical condensation apply root canal cement or sealer around the individual cones or in between segments as a binding agent.

Another method employs an injection gun that injects warm or hot gutta percha filling material into a root canal. The injector initially places heated gutta percha at the seat of the root canal which is then condensed with a plugger into the root tip. The injector then backfills the root canal by injecting additional gutta percha into the root canal until it is obturated. A similar method involves heating gutta percha on a flexible metal carrier used to insert the gutta percha into the root canal. The carrier may be a solid rod, or a hollow rod, situated in the center of a master cone. The rod is connected to a handle which may be removed by slipping it out of the hollow rod, or cutting it off if it is a solid rod. While these systems provide for convenient and quick obturation of the canal, they pose a removal problem for the dentist who has to place a post.

Of all the methods used for obturating a canal, there is no device currently available that will allow a doctor to simultaneously obturate a root canal and place an endodontic post. Currently, an endodontist will perform the root canal procedure and the obturation during one patient visit. After the canal is obturated and temporarily sealed, the patient is frequently treated by a second dentist who will place the post. To do so, the gutta percha has to be removed from the canal until only a portion 5 mm or so from the apex remains to act as an apical seal. The rods inside the current systems make gutta percha removal much more difficult since the coronal portion of the gutta percha rod has to be removed to allow for the placement of the endodontic post. One way to overcome this problem has been to notch the obturating rod with a bur. Then, when the obturator is placed in the canal it is twisted, snapping off the apical portion. The longer coronal portion is removed. It is then re-introduced into the canal and the gutta percha is stripped off by means of pulling the rod through an endodontic stop. Since the endodontic stop is extremely narrow, the gutta percha is pulled from the rod as it is withdrawn and the gutta percha remains in the canal. It is subsequently condensed. As a result of this technique, the restoring dentist does not have to deal with the rod and only has to remove the gutta percha to make room for the post. Some gutta percha may remain on the walls of the canal jeopardizing the bond strength of the post the radicular dentin. Reinfection of the treated tooth can be a problem because the endodontist performing the root canal procedure will seal the coronal opening with a temporary stopping agent which can leak oral fluids carrying bacterial into the canal opening.

It is desirable to reduce the steps and time involved in performing obturation and placement of a post in a root canal. It would be beneficial to limit the obturation and post placement to a single visit to the dentist or prosthodontist. It is advantageous to reduce and/or eliminate the leakage problems associated with poor sealing at the coronal end of the canal.

SUMMARY OF THE INVENTION

These and other objects and advantages are accomplished by the endodontic post of the present invention comprising a combined endodontic post and tip of filling material such as thermoplastic material in a single unit. To use the post unit, the tip of the device is softened by placing in an oven or heater to heat and soften the filling material or chemically treating to soften the material. The device will then be placed in a root canal that has been opened to a predetermined dimension by use of endodontic files, to seal the apical end. If necessary, the gutta percha can be compacted toward the apex, while it is still in the softened state, to ensure the apex is adequately sealed. The post may then be cemented into place by lining the canal walls with a bonding agent and filling the interface between the post and the walls of the canal with a resin cement such as a dual cure cement, a light cure cement or a self cure cement such as Lute-It® dual cure luting cement or Cement-It® Universal cement, both available from Jeneric/Pentron Inc., in Wallingford, Conn. This will result in a coronal seal of the canal via resin restorative material and an apical seal of the canal by means of gutta percha and sealant. The remaining portion of the post, extending supra-gingivally, will be used to build a core around it. Any excess will be cut off. One length of the device will be longer to accommodate the longer roots in anterior teeth. Another length will be shorter to accommodate smaller roots in the molar region. Various diameters may also be provided to accommodate the different sizes of root canals. The bonded flexible post may strengthen the tooth to prevent subsequent root fractures.

BRIEF DESCRIPTION OF THE DRAWINGS

Features of the present invention are disclosed in the accompanying drawings, wherein similar reference characters denote similar elements throughout the several views, and wherein:

FIG. 1 is an elevational view of a post in accordance with the invention;

FIG. 2 is an elevational view of a post with an alternate carrier in accordance with the invention;

DESCRIPTION OF THE INVENTION

Figure 3:
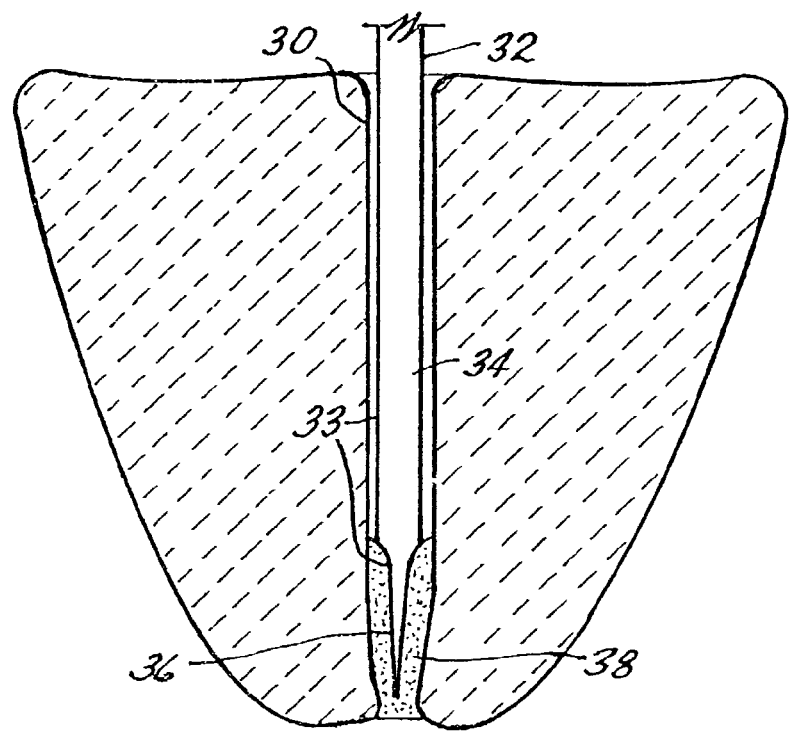
FIG. 3 is a sectional view of a tooth showing a post of the invention placed in the root canal.

As will be appreciated, the present invention provides a combination endodontic post and filler cone in a single unit. Reference is made to FIGS. 1 and 2 which show a post unit 10 comprising a post section 11 and a cone or tip section 14. Tip section 14 comprises a flexible rod or cone of biocompatible material for filling the apex of the canal. The filling material is typically a thermoplastic, chemo-plastic (i.e., may be softened by chemicals), resinous or similar polymeric material, such as gutta percha and is attached to post section 11 at the apical end 10a. Other examples of thermoplastic materials include but are not limited to polyacrylates such as polymethyl methacrylate, polyhydroxy ethyl methacrylate, and hydroxy ethyl methacrylate (HEMA), polyurethanes, polypropylene, polyethylene, polyamides, fluoropolymers such as Teflon® PTFE and Teflon® PFA, polyesters such as polylactic acid, glycolide and polycaprolactone and their co-polymers, polyphosphazenes, polyanhydrides, polysulfides, polyethers, epoxies, polycarbonates, polystyrene, polybutadiene, polyphenylene oxide, and silicone rubber materials such as polysiloxanes.

The filling material may include additives typical in the dental field such as plasticizing, antibiotic, cariostatic, antibacterial, or other anti-inflammatory, biologically active or therapeutic materials.

Post section 11 comprises a main body or endodontic portion 12 and a carrier or apical portion 13 which is located at the apical end 10a of post unit 10. Main body 12 may be a solid rod of circular or other suitable cross-section comprising a substantially smooth surface or may comprise a plurality of frustoconical sections 16 arranged coaxially along the longitudinal axis of main body 12. Preferably, main body 12 has consistent width along the longitudinal axis thereof whereas frustoconical sections 16 each have the same tapered width and same length. It is possible to vary the width and/or length of main body 12 and/or vary the tapered width and/or length of frustoconical sections 16 along the longitudinal axis of main body 12. Main body 12 may include a larger head of any shape with or without a retentive design to provide support for a core thereon at the supracoronal end 12h as will be discussed hereinafter.

Carrier 13 is preferably an extension of main body 12 of post section 11 and is of very fine diameter to accommodate tip section 14 of thermoplastic material of post unit 10. In one method of manufacture which will be discussed hereinafter, post section 11 is manufactured from a rod of material that is cut or machined at the apical end 10a to result in carrier 13 having a very small width or diameter in comparison to main body 12. Carrier 13 is of small diameter to allow enough area to form tip section 14 thereon, and also of enough strength and integrity to accommodate the filling material such as thermoplastic material. As stated above, carrier 13 is preferably an extension of main body 12 and is shown having constant diameter along the length thereof, but may be of any shape or size sufficient to hold tip section 14 thereon. FIG. 2 shows an alternative carrier 13 of tapered width.

Post section 11 may be fabricated of any material to provide a flexible apical portion and a more rigid endodontic and/or coronal or supracoronal portion, such as metal, plastic, ceramic, polymeric, composite, or other material suitable for placement in the mouth. Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference. The fiber reinforced composite material may comprise fibers in the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional, or randomly dispersed, and may be as short as about 3 to about 4 millimeters (mm) or shorter. The fibers may also be in the form of fabric as set forth in copending Ser. No. 09/280,760 filed Mar. 29, 1999 and may include any of the attributes of the post described therein, the contents all of which are hereby incorporated by reference. Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the device is comprised of unidirectional microfilamentous glass fibers bundled in a resin matrix.

In order to enhance the bond between the fibers and polymeric matrix, thereby enhancing the reinforcing effect, the fibers may be silanized or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, New York The polymeric matrix is selected from those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Fillers may be present in addition to or instead of fibers in an amount up to about 80 wt %, and preferably about 70 wt %. If fibers are present, the amount of filler is present in an amount of up to about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates. If the post is manufactured from a composite material, it is preferably in completely cured or hardened state.

Examples of metals useful as post section 11 include but are not limited to metals or alloys of Pd, Pt, Rh, Ir, Au, Ag, Ti, Co, Mo and mixtures thereof such as AgPd, AuPtPd, TiAlFe, TiAlV, CoCrMo, stainless steel and brass. Ceramic materials useful in the fabrication of post section 11 include but are not limited to alumina, zirconia, mullite, spinel, porcelain, titania, lithium disilicate, leucite, amorphous glass, lithium phosphate, and combinations thereof, or any high strength ceramic material which can withstand the stresses created in the mouth.

In accordance with one method of manufacture herein, post section 11 (which includes main body 12 and carrier 13) is manufactured in any known method in the art and depending upon the material used for the manufacture of post section 11. Such methods include but are not limited to matched die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. As discussed above, post section 11 is formed into a rod-shaped unit or main body 12 having a very fine or thin apical end or carrier 13. The final shape of post section 11 may be formed simultaneously during the manufacturing process thereof. Alternatively, a rod shaped material may be manufactured and thereafter shaped by grinding, cutting, milling or the like into the desired shape and size. As shown in FIGS. 1 and 2, post section 11 is a rod-shaped component having a main body 12 comprising slightly tapered stepped sections 16, all of the same dimensions and whereby one end of post section 11 comprises a very narrow section, 13, which acts as the carrier for the filling material. As with sections 16, carrier 13 may be formed during the actual manufacture of main body 12 or thereafter by grinding, cutting or similar means. Although main body 12 includes sections 16 to aid in the retention of the post in the canal, main body 12 may be of any surface (e.g., smooth, partly smooth and partly frusto-conical,) and shape suitable for placement in the canal such as in the case of smaller diameter posts whereby the ledges may be eliminated so as to maintain the structural integrity and strength of the post. Carrier 13 preferably comprises a smooth surface, although it is in no way limited to such and may be of any surface suitable for application of filling material thereon. The post may be provided in an opaque tooth color or it may be colored similar to a tooth's pulp for enhanced esthetics. The post may include an appropriate amount of raadiopaque material such as titanium oxide, barium sulfate, and similar materials known in the dental industry to insure x-ray documentation which may be added to the post material during manufacture thereof.

After post section 11 has been manufactured, carrier 13 of post section 11 is then coated with a filling material such as gutta percha to obtain cone section 14 thereon. The filling material may be applied by any known means such as dipping, injection molding, hand rolling, and the like.

The length of post unit 10 may vary depending upon the length of the root into which it will be inserted. It is preferable that post 10 be manufactured in a variety of lengths and widths to fit the many different root canals of dental patients and the differing lengths of the anterior (central and lateral incisors, bicuspids and premolars) and molar teeth. Preferably, post unit 10 is about 14 to about 31 mm in length and more preferably about 16 to about 25 mm in length. For the length parameter, post section 11 may be divided into three sections. Section 13 is the apical section and is about 3 to about 12 mm in length and preferably about 5 to about 8 mm in length. If section 13 is tapered as in FIG. 2, the taper may be continuous at about 0.02 mm/per mm or less from the apical tip 13*t* to the end 13*e* of carrier 13, or preferably 0.04 mm/per mm from the apical tip 13*t* to the end 13*e* of carrier 13. As stated above, carrier 13 is covered with a filling material such as a thermoplastic material which does not extend more than a few mm in length past the tip of 13 (13*t*). Main body 12 comprises a main section from point 13*e* to point 12*m* which is about 5 to about 13 mm in length and preferably about 7 to about 11 mm in length, and a supracoronal portion or "head" of post section 11 from point 12*m* to point 12*h* which about 2 to about 8 mm and more preferably about 4 to about 6 mm in length. The supracoronal portion of post unit 11 will be used to build a core upon which a crown will be placed. The main section (from 13*e* to 12*m*) of main body 12 of post section 11 may be slightly flexible to negotiate curved canals.

The diameter of post section 11 will also vary and range from about 0.02 to about 0.15 at the apical end (13*t*–13*e*) and preferably from about 0.02 to about 0.09 at the apical end (13*t*–13*e*). If carrier 13 is tapered, the diameter at 13*t* is in the range of about 0.02 to about 0.15 and preferably about 0.05 to about 0.1 mm and the diameter at 13*e* is in the range of about 0.2 to about 0.6 and preferably about 0.25 to about 0.4 mm. At the supracoronal end, the diameter is about 0.4 to about 2.0 and preferably about 0.5 to about 1.75 mm.

Tip section 14 comprising the filling material is about 0.5 to 1 mm longer than carrier 13, but the diameter of tip section 14 is tapered from point 13*e* to point 13*t* in accordance with ISO standards to correspond to current obturating techniques utilizing master cones of thermoplastic material. Accordingly, tip section 14 can be tapered at least 0.02 mm/per mm in accordance with ISO standards, and preferably 0.04 or 0.06 mm/per mm, or greater, measuring from tip 14*t* to 14*e*, for insertion into canals created with 0.02, 0.04, 0.06, or greater, tapered files. The diameter of tip 14 at point 14*e* is in the range of about 0.30 to about 2.0 mm and preferably 0.40 to about 1.5 mm. The diameter of tip 14 at point 14*t* is in the range of about 0.20 to about 1.0 mm and preferably about 0.25 to about 0.80 mm. When using the post unit in canals of 0.02 taper, the filling material such as thermoplastic material will be compressed by the canal and forced toward the coronal end of the canal. This will result in an apical seal in excess of 8 mm. The excess thermoplastic material can be removed with a heated instrument after it has hardened. When using the post unit in 0.06 tapered canals, the filling material can be condensed down toward the apex to fill the void created by the greater taper. This will result in an apical seal less than 8 mm, but in excess of 4 mm which is sufficient to maintain the apical seal.

To use the post unit, the device is placed in or near an oven or heater to heat and soften the filling material or dipped in a chemical solution such as chloroform to soften the filling material. The device will then be placed in a root canal that has been opened to a predetermined dimension by use of endodontic files, to seal the apical end. If necessary, the gutta percha can be compacted toward the apex, while it is still in the softened state, to ensure the apex is adequately sealed. The post is then cemented into place by lining the canal walls with a bonding agent and filling the interface between the post and the walls of the canal with a resin cement, such as a dual cure cement. This will result in a coronal seal of the canal via resin restorative material and an apical seal of the canal by means of gutta percha and sealant. The remaining portion of the post, extending supra-gingivally, will be used to build a core around it, and if necessary, for placement of a crown thereon. Any excess of the post will be cut off. One length of the device will be longer to accommodate the longer roots in anterior teeth. Another length will be shorter to accommodate smaller roots in the molar region.

FIG. 3 shows a root canal 30 with post unit 32 therein. Post unit 32 comprises a post section 33 having a main body 34 and a carrier 36 that carries the filling material 38. As shown in FIG. 3, the thermoplastic material 38 was softened prior to insertion and fills the apex of the canal.

Figure 4:
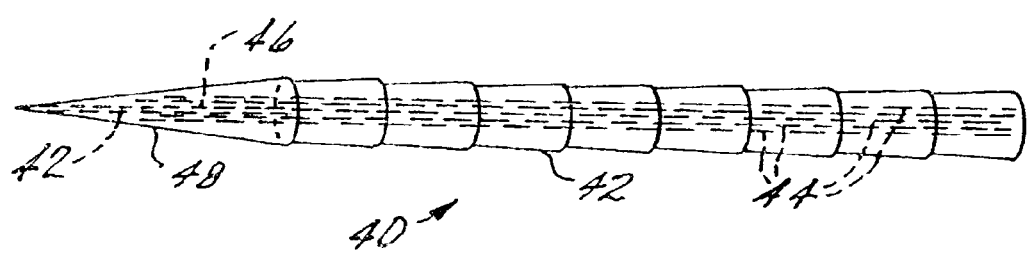
FIG. 4 is an elevational view of an alternate embodiment of a post in accordance with the invention.

In an alternate embodiment herein, reference is made to FIG. 4 wherein a post unit 40 comprises a post section 42 fabricated of fiber reinforced composite material wherein the fibers comprise optical fibers 44 such as glass fibers or a central core of a material such as metal which is able to transmit heat energy to the filling material. Glass fibers 44 extend out through post section 42 into carrier 46 and tip section 48. To use the post unit 40, the filling material 48 does not have to be softened or heated prior to insertion into the canal. Post unit 40 is inserted into the canal with tip 48 in its hardened state. A curing light or other heat source is applied to the coronal portion of the post, transmitting light or heat down toward the apex. Fibers 44 convert the light into heat or, alternatively, the core section transmits heat to the filling material. The heat then plasticizes the filling material such as gutta percha at the apex. The post is then pushed toward the apex using gentle finger pressure. This last step insures that the plasticized gutta percha is compressed apically and laterally, sealing the tooth and any lateral canals.

One of the benefits of this alternative embodiment is that it insures plasticized gutta percha is only introduced to the apical portion of the root and that the coronal portion of the root is free of gutta percha which could negatively affect the retentive strength of the post/core.

Figure 5:
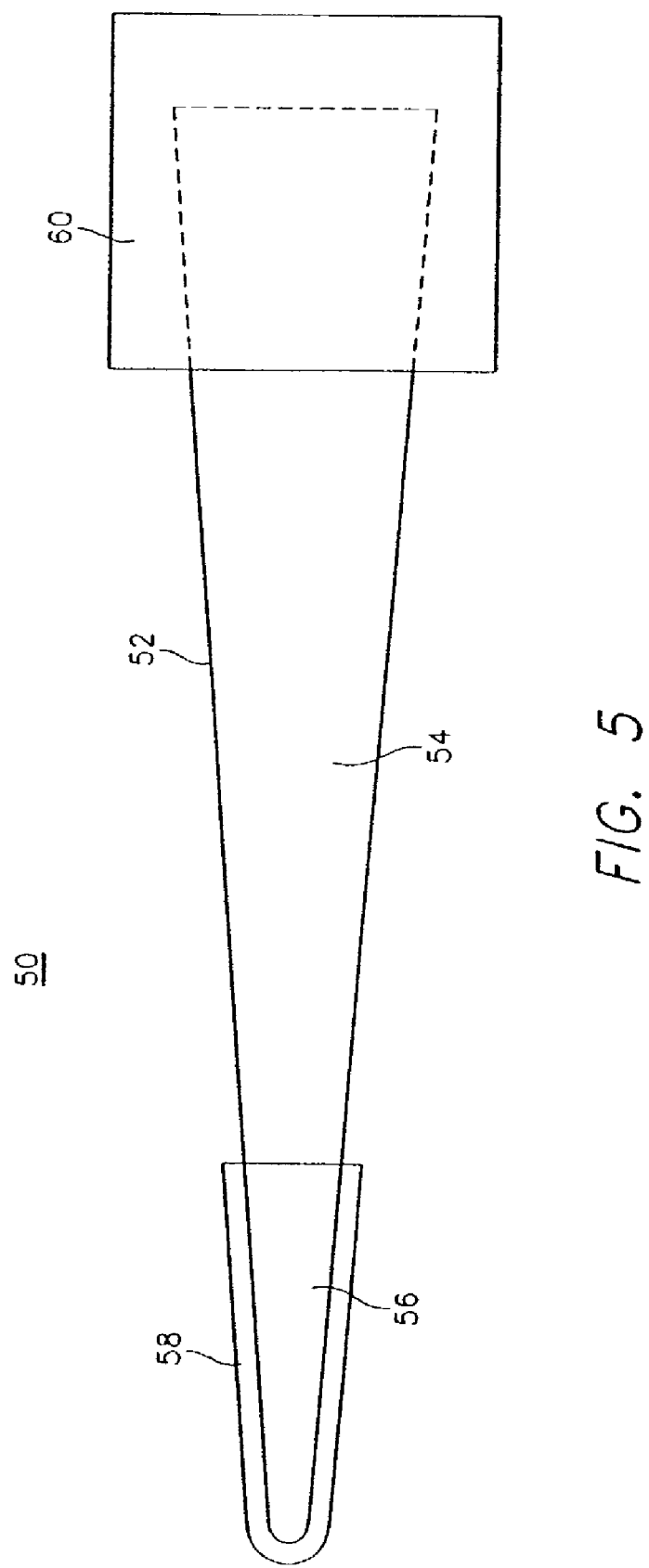
FIG. 5 is an elevational view of an alternate embodiment of a post in accordance with the invention.

In yet another embodiment herein, reference is made to FIG. 5 wherein a post unit 50 comprises a post section 52 fabricated of fiber reinforced composite material. Post section 52 includes main body 54 and carrier 56. Carrier 56 is coated with a filling material such as gutta percha to obtain cone section 58 thereon. As shown in the drawing, main body 54 is tapered to provide ease of placement into the canal. The cross-section of post unit 50 may be smaller than the cross-section of a standard post to fit in thinner or smaller auxiliary canals which are normally filled with a thermoplastic material. Accordingly, post unit 50 can act as an obturator. As an obturator, better support is provided due to the fiber-reinforced composite structural component 54 upon which cone section 58 is applied in comparison to using only a thermoplastic material as an obturator. Moreover, the obturator may be easily cemented in place in the canal. The size of post unit 50 is about 15 to about 30 mm in length with a diameter in the range of about 1.0 to about 1.75 mm. The taper of the post unit is about 0.02 to about 0.06 mm/per mm. Although carrier section 56 is shown as being tapered, it may also be of constant diameter. Post unit 50 may also include a handle 60 which is beneficial when the post unit is used as an obturator. Section 54 of unit 50 within handle 60 may be tapered or straight. Handle 60 may be any filled or unfilled polymeric material, such as those mentioned above and used in the fabrication of the post.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains.

Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An endodontic post comprising:
   a post section; the post section comprising a rigid endodontic section and a tip section, wherein the tip section is a flexible carrier surrounded by a filler cone; and wherein the filler cone comprises polyacrylate, polyurethane, polypropylene, polyethylene, polyamide, fluoropolymer, polyester, polyphosphazene, polyanhydride, polysulfide, polyether, epoxy, polycarbonate, polystyrene, polybutadiene, polyphenylene oxide, silicone rubber or a mixture thereof.

2. The endodontic post of claim 1 wherein the polyacrylate comprises polymethyl methacrylate, polyhydroxy ethyl methacrylate, or hydroxy ethyl methacrylate (HEMA).

3. The endodontic post of claim 1 wherein the fluoropolymer comprises Teflon® PTFE or Teflon® PFA.

4. The endodontic post of claim 1 wherein the polyester comprises polylactic acid, glycolide, polycaprolactone or a co-polymer thereof.

5. The endodontic post of claim 1 wherein the silicone rubber comprises polysiloxane.

6. The endodontic post of claim 1 wherein the flexible carrier is integral to the post section.

7. The endodontic post of claim 1 wherein the post section comprises an apical portion and an endodontic portion and wherein the apical portion comprises the flexible carrier.

8. The endodontic post of claim 7 wherein the apical portion of the post is narrower in diameter than the diameter of the endodontic portion.

9. The endodontic post of claim 7 wherein the post further comprises a supracoronal portion.

10. The endodontic post of claim 1 wherein the post section is fabricated of metal, plastic, composite, ceramic, glass or polymeric material.

11. An endodontic post comprising:
    a post section; the post section comprising a rigid endodontic section and a tip section, wherein the tip section is a flexible carrier surrounded by a filler cone; and wherein the filler cone comprises a plasticizing agent, antibiotic agent, cariostatic agent, antibacterial agent, anti-inflammatory agent, biologically active agent, or therapeutic agent, or mixture thereof.

12. A method for restoring the root canal of a toot comprising:
    preparing the root canal;
    providing a post for insertion into the canal, whereby the post comprises a post section, the post comprising a rigid endondontic section and a tip section, wherein the tip section is a flexible carrier surrounded by a filler cone;
    inserting the post into the canal, whereby the root canal is scaled by the filling material.

13. The method of claim 12 further comprising inserting a sealing material into the canal to bond the post to the canal.

14. The method of claim 12 further comprising building a core on an end of the post that extends from the canal.

15. The method of claim 14 further comprising placing a crown on the core.

16. An obturator comprising:
    a post section;
    wherein the post section is tapered; and
    a wherein the post section comprises a rigid endodontic section and a tip section;
    wherein the tip section is a flexible carrier surrounded by a filler cone; and
    wherein the filler cone comprises polyacrylate, polyurethane, polypropylene, polyethylene, polyamide, fluoropolymer, polyester, polyphosphazene, polyanhydride, polysulfide, polyether, epoxy, polycarbonate, polystyrene, polybutadiene, polyphenylene oxide, silicone rubber or a mixture thereof.

17. The obturator of claim 16 wherein the polyacrylate comprises polymethyl methacrylate, polyhydroxy ethyl methacrylate, or hydroxy ethyl methacrylate (HEMA).

18. The obturator of claim 16 wherein the fluoropolymer comprises Teflon® PTFE or Teflon® PFA.

19. The obturator of claim 16 wherein the polyester comprises polylactic acid, glycolide, polycaprolactone or a co-polymer thereof.

20. The obturator of claim 16 wherein the silicone rubber comprises polysiloxane.

21. The obturator of claim 16 further comprising a handle.

22. The obturator of claim 16 wherein the flexible carrier is integral to the post section.

23. The obturator of claim 16 wherein the post section comprises an apical portion and an endodontic portion and wherein the apical portion comprises the flexible carrier.

24. The obturator of claim 23 wherein the apical portion of the post is narrower in diameter than the diameter of the endodontic portion.

25. The obturator of claim 16 wherein the post section is fabricated of metal, plastic, composite, ceramic, glass or polymeric material.

26. An obturator comprising:
    a post section;
    wherein the post section is tapered;
    wherein the post section comprises a rigid endodontic section and a tip section;
    wherein the tip section is a flexible carrier surrounded by a filler cone; and
    wherein the filler cone comprises a plasticizing agent, antibiotic agent, cariostatic agent, antibacterial agent, anti-inflammatory agent, biologically active agent, or therapeutic agent, or mixture thereof.

27. The obturator of claim 26 further comprising a handle.

* * * * *